United States Patent
Doyen

(10) Patent No.: US 7,812,616 B2
(45) Date of Patent: Oct. 12, 2010

(54) SYSTEMS AND METHODS FOR DETECTING VARIATIONS IN COMPOSITE STRUCTURES

(75) Inventor: William George Doyen, Annapolis, MD (US)

(73) Assignee: Arinc Incorporated, Annapolis, MD (US)

(*) Notice: Subject to any disclaimer, the term of this patent is extended or adjusted under 35 U.S.C. 154(b) by 1023 days.

(21) Appl. No.: 11/585,120

(22) Filed: Oct. 24, 2006

(65) Prior Publication Data

US 2008/0094273 A1 Apr. 24, 2008

(51) Int. Cl.
*G01R 27/04* (2006.01)

(52) U.S. Cl. ........................ 324/637; 324/647; 324/526

(58) Field of Classification Search ................ 324/526, 324/637, 647
See application file for complete search history.

(56) References Cited

U.S. PATENT DOCUMENTS

| | | | |
|---|---|---|---|
| 4,494,408 A | 1/1985 | DeLacy | |
| 4,836,030 A | 6/1989 | Martin | |
| 4,871,255 A | 10/1989 | Tenjinbayashi | |
| 5,562,788 A | 10/1996 | Kitson et al. | |
| 5,786,691 A | 7/1998 | Palmer, Jr. et al. | |
| 6,031,498 A | 2/2000 | Issler | |
| 6,181,285 B1 | 1/2001 | Sullivan et al. | |
| 6,424,165 B1 | 7/2002 | de Boer et al. | |
| 6,698,288 B2 | 3/2004 | Shirzad et al. | |

*Primary Examiner*—Vincent Q Nguyen
(74) *Attorney, Agent, or Firm*—Oliff & Berridge, PLC

(57) ABSTRACT

A system and method to detect changes in composite structures using RF signal pattern data interpretation. An RF signal is transmitted from a composite material manufactured structure and a plurality of sensors are employed to measure the RF signal. The measured RF signal is compared to a stored baseline RF signal for the particular structure. Deviations in the measured RF pattern for the structure, or for a structurally-similar composite structure, are automatically analyzed to detect non-visually-detectable defects or other changes in the composite structure. A baseline RF signature is developed for a structure by transmitting a reference RF signal from the composite structure. RF signals are detected by a variety of methods, and the detected signals are compiled and translated into reference and/or test RF signal patterns for the structure.

20 Claims, 3 Drawing Sheets

SYSTEMS AND METHODS FOR DETECTING VARIATIONS IN COMPOSITE STRUCTURES

BACKGROUND

This disclosure is directed to systems and methods for detecting variations in composite structures using radio frequency (RF) transmission.

Composite materials, as discussed in this disclosure, refer to a class of materials that are prepared by combining two or more materials having different physical properties. Specifically, composite materials are those in which the different materials are combined in a manner such that they work together to optimize certain properties. These properties include, but are not limited to, lighter weights, increased strength and improved corrosion resistance. Such composite materials generally consist of a matrix or binder that surrounds, and bonds together, clusters of fibers that may be, for example, laminated in layers. In a layered configuration, each layer may have fibers arranged within the layer such that a principal direction of the fiber matrix is orthogonal to an arrangement of the fibers in an adjacent layer. Such an arrangement in the finished composite material yields increased strength and added fracture resistance in two orthogonally planar directions.

Composite materials, as discussed above, are generally those obtained by joining two or more materials, or two or more layers, by physical or chemical bonding methods. Composite materials may be formed in solid, laminated or laminated core constructions. The capacity of composite materials to exhibit improved strength to weight ratio characteristics make the use of these materials desirable in a number of applications where increased strength, resilience and flexibility of construction are desired. General fields in which the use of composite materials have gained wide acceptance include sporting goods, watercraft, automobiles, aircraft and spacecraft. Composite materials are, however, also applicable in other structures such as, for example, water towers and any manner of containers.

Composite materials, therefore, exhibit several advantageous characteristics. In the face of these advantages, a problem has been noted with composite materials, related to safety and/or consistency in manufacturing, with regard to structures manufactured from these materials. The difficulty is that, although structurally stronger than many of the materials from which like structures may have been traditionally manufactured, composite materials exhibit generally very limited elastic deformation. Though highly resistant to failure, when failure occurs, it is generally catastrophic. Such a disadvantage is particularly acute in the area of aircraft and spacecraft, where the use of composites has become more widespread, and where catastrophic structural failure may have most dire consequences.

The above difficulties are exacerbated by the fact that defects, changes, and/or damage to composite structures or composite components within structures are characteristically more difficult to detect with most conventional means.

Inspection of composite materials, composite material structures and/or composite material components is complicated, in a first instance, due to a general lack of any appreciable visible indicator of stress, deformation or other like indicator typically relied upon in structures manufactured from other materials to indicate potential for impending failure. Based on the generally layered and/or laminated nature of composite materials for use in structures and/or components, any "evidence" of impending failure may only lie in, for example, internal micro-fractures that may exist below the visible surface of the structure or component surface. As such, composite material failure is further particularly dangerous because composite material structures may often fail to exhibit any visibly-detectable signs of fatigue before complete failure.

As composite materials find utility in significantly broader applications, and the sheer number of structures manufactured from composite materials grows, and where, in particular, composite materials are employed in structures in which non-predictable and non-detectible catastrophic material failure may occur, the above-identified shortfall, and the effects thereof, become particularly more acute. For example, as the size of the fleet of new aircraft with composite material structures and components grows, and moreover, where a vast number of those components and structures age with use and wear, an ability to inspect the composite structures and components, particularly those used in aircraft, in a reliable manner, grows.

SUMMARY

Numerous methods are conventionally employed to routinely and/or periodically inspect structures to detect indications of stress, fatigue or other evidence of impending failure. A general class of non-destructive inspection (NDI) methodologies includes, for example, tap testing, x-ray testing, laser testing, thermal imaging testing, and resistance to an applied physical force testing. Each of the above-described methods, although well-known and well-understood with regard to advantages and disadvantages of other employment for NDI of conventional material-manufactured structures, has attendant shortfalls with regard to employment in the field of composite materials. These testing techniques all have shortfalls with respect to accuracy. These techniques, in many cases, are more an art than a science, and very dependent on the experience and skill of the tester. Additionally, these methodologies often lack clear and unambiguous pass/fail criteria. To date, none of the known methods can be used individually to reliably test for defects, damage and/or changes in composite material manufactured structures under all circumstances. Accordingly, there is a continued need for improved methods of detecting defects, damage and/or other changes in composite material manufactured structures.

Based on the widespread acceptance of composite materials in the manufacture of myriad structures, and a need in the face of the unique non-visually-detectable failure potential of these materials, there is a significant need to find a reliable, cost effective and accurate method by which to non-destructively inspect these structures on a routine and/or periodic basis.

In other words, it would be advantageous, in light of the above-identified shortfalls in other NDI systems, particularly as they relate to composite material inspection, to provide systems and methods by which defects, damage and/or changes in composite material manufactured structures could be more reliably and effectively detected.

In various exemplary embodiments, the systems and methods according to this disclosure are directed, for example, to detecting changes in particular structures over time and detecting variations among similar structures, by transmitting RF signals from, on, within, or in proximity to, the structures, detecting the transmissions, and comparing aspects of one or more received transmissions to determine areas of potential material failure in composite material manufactured structures.

In various exemplary embodiments, the systems and methods according to this disclosure, detect subtle, localized variations or shifts in the structure of a body manufactured from a composite material using RF pattern detection, measurement, comparison and analysis In various exemplary embodiments, the systems and methods according to this disclosure may transmit an RF signal from a composite structure under test, or in proximity to a composite structure under test. A plurality of sensors may then be employed to measure the RF signal emanating from, or otherwise related to, the composite structure under test. The measured RF signal may be then compared to a stored baseline RF signal for the particular structure under test. Deviations in the measured RF pattern for the structure under test, or a structurally similar composite structure, may then be analyzed to determine that the differences are based on a non-visually-detectible defect, state of damage, and/or change in the composite structure.

In various exemplary embodiments, a baseline RF pattern may be developed for a structure by transmitting a reference RF signal from or in proximity to a composite material manufactured structure. The reference RF signal may be detected by a variety of methods from a plurality of points in proximity to the composite structure. The detected signals may be compiled and translated into a reference RF pattern for the structure. The reference RF pattern may then be stored for various potential future uses, including later pattern comparison and analysis to detect material changes through detection and analysis of changes in the RF patterns of the structure.

In various exemplary embodiments, a reference RF signal is transmitted from or in proximity to a reference composite structure. The reference RF signal is detected from at least one point proximate to the reference composite structure. The detected reference RF signal is compiled into a reference RF pattern. A test RF signal is, at some time later, transmitted from or in proximity to a composite structure under test. The test signal is detected from at least one point proximate to the composite structure under test. The detected test RF signal is compiled into a test RF pattern. Characteristics of the test RF pattern are compared to the characteristics of the reference RF pattern. Differences in characteristics of the test RF pattern and the reference RF pattern are analyzed and output.

In various exemplary embodiments, the reference signals are detected from a plurality of points proximate to the composite structure, the plurality of points lying in a two-dimensional plane, the plane being movable relative to the composite structure or in three dimensional space.

The systems and methods according to this disclosure are intended to address attendant shortfalls in other NDI methodologies by providing, among other advantages:

objective empirical comparison with previously known failure modes and comparison with other units within a class of structures such as, for example, other aircraft tested, enabling further investigation of structures that deviate from reference values by more than a pre-determined threshold;

capacity to collect and expand data samples to improve accuracy of, and insight into, the testing methodology, and characterization of the aging of structures under test faster test results and an ability to automatically isolate a particularly anomalous location within a composite structure and to potentially immediately characterize the nature of the anomaly;

enhanced failure prediction with a disciplined scheme for repetitive testing of a same composite structure that is more likely to detect otherwise undetectable changes in key components earlier and well before catastrophic failure occurs; and other miscellaneous advantages including, but not limited to, ease of test setup and execution, reproducible and reliable results, greater accuracy, low reliance on the skill of the tester, easy test documentation, low cost, and enhanced post-test analysis over time as new information is obtained.

The systems and methods according to this disclosure may be employed alone, or in concert with other conventional testing methodologies, such as those listed above, to enhance overall safety by cooperative failure prediction based on a combination of such methods.

These and other objects, advantages and features of the systems and methods according to this disclosure are described in, or apparent from, the following description of embodiments.

BRIEF DESCRIPTION OF THE DRAWINGS

Various exemplary embodiments of the disclosed systems and methods will be described, in detail, with reference to the following figures, wherein.

DETAILED DESCRIPTION OF EMBODIMENTS

The following description of various exemplary embodiments of systems and methods for detecting variations in composite structures using RF signals may refer to and/or illustrate one specific type of detection system for the sake of clarity and ease of depiction and description. However, it should be appreciated that the principles disclosed herein, as outlined and/or discussed below, can be equally applied to any known, or later-developed, system in which variations in detected RF signal patterns may be used to determine variations in composite material manufactured structures.

Figure 1:
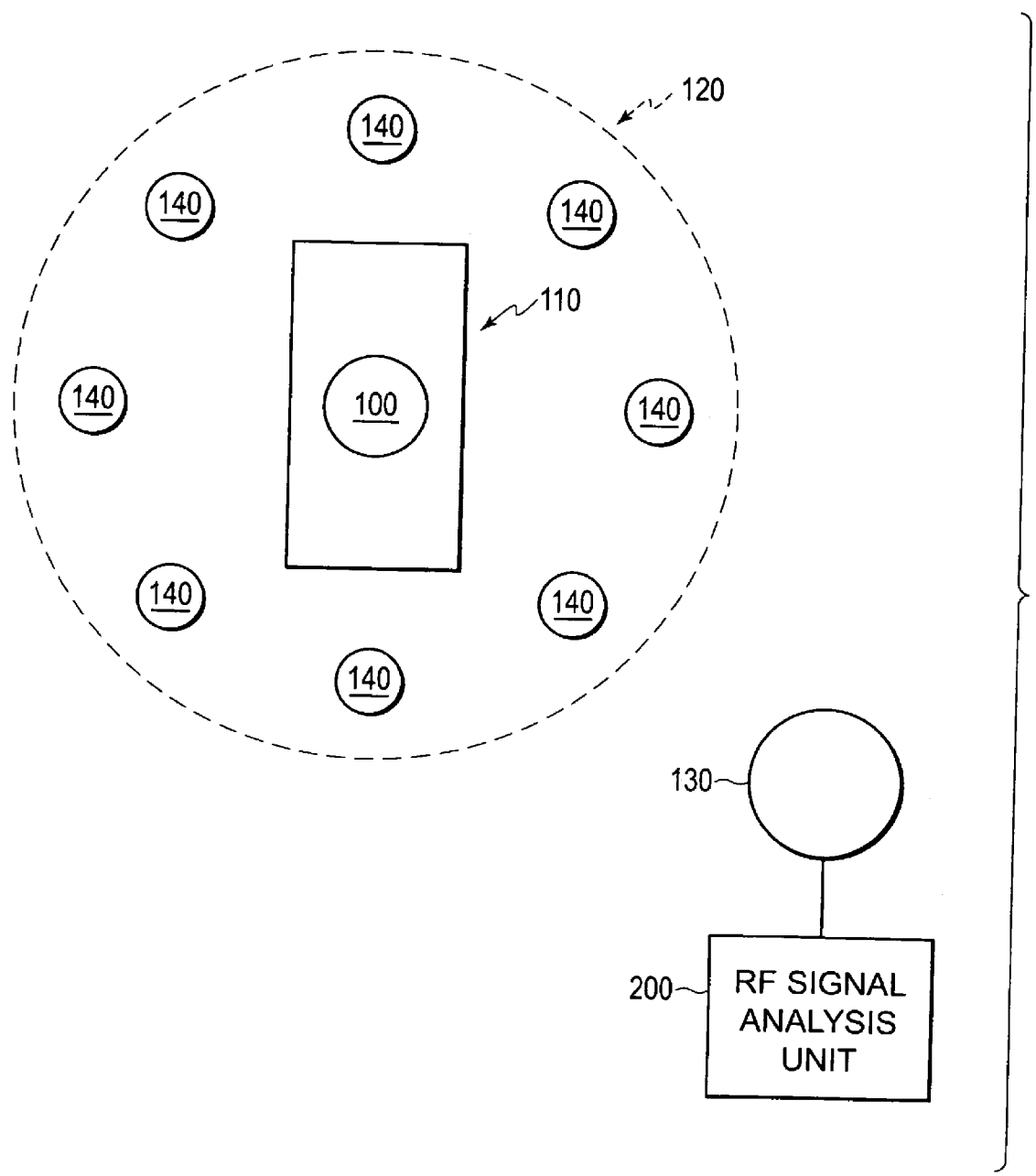
FIG. 1 schematically illustrates an exemplary embodiment of a system for detecting changes in composite material manufactured structures using RF signals.

FIG. 1 schematically illustrates an exemplary embodiment of a system for detecting changes in composite structures using RF signals. As shown in FIG. 1, an RF signal transmitter 100 is placed on or otherwise installed within a structure manufactured at least in part of one or more composite materials, and/or containing one or more composite components, hereinafter composite structure 110. It should be appreciated that the RF signal transmitter 100 may alternatively be placed in a location proximate to, rather than on or in, the composite structure 110. The RF signal transmitter 100 is provided to transmit a specified RF signal 120 from, or in proximity to, the composite structure 110.

One or more RF signal detection units 140 are placed in such a manner to detect the emitted RF signal 120. Although shown in the plane of the depiction in FIG. 1, it should be appreciated that RF signal detection units 140 may be positioned in any of multiple dimensions spatially around the composite structure 110. Additionally, the RF signal detection units 140 need not be fixedly held in any specific position but rather, may be moveable in any direction around the composite structure in such a manner to randomly or continuously detect an emitted RF signal with relation to one or more specific discrete portions of the composite structure 110, or otherwise with relation to the entire composite structure 110. For example, a single RF signal detection unit 140 could be moved from location to location to collect all of the RF signal data.

RF signal detection units 140 may then be employed to transmit the detected RF signals to, for example, an RF signal collector 130. It should be appreciated that any methodology by which an RF signal my be transmitted from, for example, a specifically-designed RF signal detection unit 140 to an RF signal collector 130 may be employed. Such data transmission may include, but not be limited to, wired or wireless data transmission. The RF signal detection units 140 may transmit raw RF data identified relative to a position of the individual RF signal detection unit 140, or the RF signal detection units 140 may include an internal capability in which detected RF signal data is converted to an output data stream including information regarding the position of the RF signal detection units 140 by which the RF signal is detected. It should further be appreciated that, in a simplest embodiment, the RF signal collector 130 may act as an RF signal detection unit 140, standing alone or in combination with a plurality of other RF signal detection units 140.

It should be appreciated that RF signal detection by a specific RF signal detection unit 140, and/or RF signal collector 130, should be properly identified with reference to a specific position of the RF signal detection unit 140, and/or the RF collector 130, relative to the composite structure 110. An emitted RF signal pattern 120, discrete portions of which are collected by, for example, RF signal detection units 140, and/or an RF signal collector 130, may be discretely, or collectively, transmitted to an RF signal analysis unit 200, which will be described in greater detail below. Again here, it is important to note that lines of data communication between, for example, RF signal detection units 140, and/or an RF signal collector 130, and the RF signal analysis unit 200 may be by any means by which such data may be effectively transmitted. Wired and/or wireless means are contemplated, as well as, if the data is compatibly modified within either of the RF signal detection units 140, and/or the RF signal collector 130, that the data may be optically transmitted to, for example, a compatible receiver in the RF signal analysis unit 200.

As will be described in greater detail below, an RF signal transmitted to an exemplary RF signal analysis unit 200 may be communicated to a recording device for recording characteristics of the detected RF signal. These characteristics may be recorded within the RF signal analysis unit 200 to be analyzed and compiled by some manner of compiler within that unit. An objective of this recording and compilation is to present the detected RF signal in a manner by which it may be compared to a stored reference RF pattern related to the same composite structure 110, or a structurally similar composite structure subjected to the same testing. That is, the RF transmitter 100, or a functionally equivalent transmitter, transmits a test signal from the same proximate location at which a reference RF signal was transmitted, which signal is received by the at least one RF signal detection unit 140 from the same proximate location at which a reference RF signal was received, the signal being recorded and compiled into as a test RF pattern. Some form of comparator may then be employed to compare characteristics of the reference pattern and the current test pattern to determine differences between the two. Comparator results may then be communicated to an output device such as, for example, a printer or display.

Figure 2:
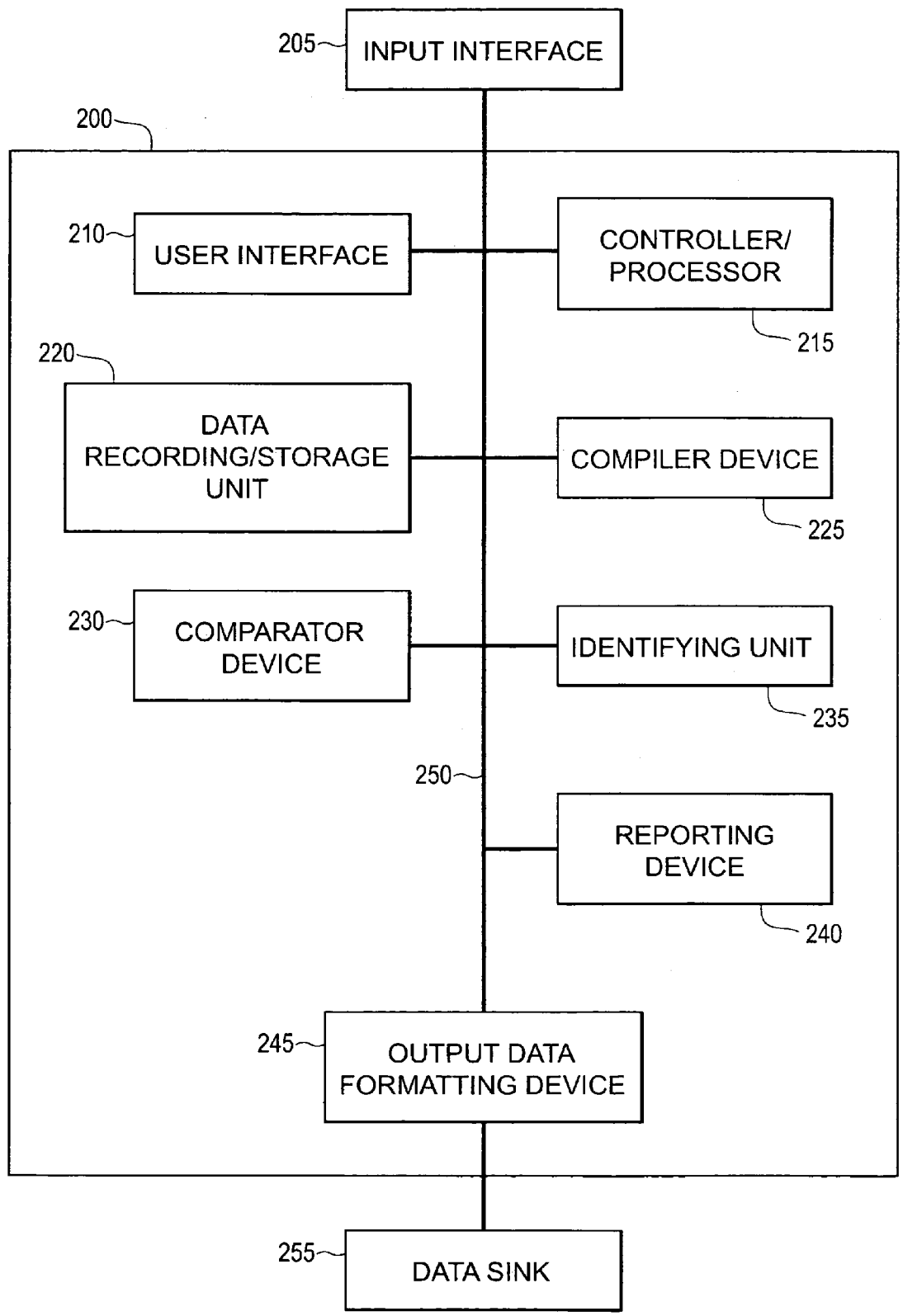
FIG. 2 is a schematic block diagram illustrating an exemplary system for implementing a method to detect changes in composite material manufactured structures using received RF signals according to this disclosure.

FIG. 2 is a schematic block diagram illustrating an exemplary embodiment of a system for implementing a method to detect changes in composite material manufactured structures using received RF signals. As shown in FIG. 2, an RF signal analysis unit 200 may include an input interface 205. This input interface may comprise a reference signal collector 130 such as that shown in FIG. 1, or another interface by which detected RF signals, including information regarding a position of one or more RF signal detection units 140, as shown in FIG. 1, may be received. The input interface 205 may receive such information in a form, or convert the information to a form, by which the RF signal analysis unit 200 may employ the collected information. Other components of the exemplary RF signal analysis unit 200 shown in FIG. 2 may include a user interface 210, a controller/processor 215, a data recording/storage unit 220, a compiler device 225, a comparator device 230, an identifying unit 235, a reporting device 240, and an output data formatting device 245, all connected by a data/control bus 250. Additionally, as will be discussed briefly below, information output from, for example, the exemplary RF signal analysis unit 200 may be transmitted to a local or remote data sink 255.

As discussed above, an RF signal transmitter 100, as shown in FIG. 1, may be located within, or proximately to, a composite structure 110 for generating an RF signal 120. At least one RF signal detection unit 140 detects the emanated RF signal and communicates characteristics of that signal to include the signal itself, as either raw or formatted data, and position information regarding the RF signal detection unit 140, to one or more devices intended to provide the information via an input interface 205 to the RF signal analysis unit 200.

The RF signal analysis unit may be manipulated by a user, or otherwise receive user input, via a user interface 210. Under control of a controller/processor 215, received RF signal data and RF signal detection unit position information, is recorded and may be stored in a data recording/storage unit 220. A compiler unit 225 compiles and analyzes the received, recorded and stored RF signal data and information to generate an RF data plot corresponding to the detected RF signal data and information from the composite structure under test. This RF data plot may be referred to as a test RF pattern.

A comparator device 230 references information regarding a stored reference RF pattern for the composite structure under test, or a structurally similar composite structure, in order to determine whether there are any, or substantial, differences in the RF patterns between the test RF pattern and the reference RF pattern. Based on this comparison, an identifying unit 235 may be available to identify portions of the composite structure under test that should be more carefully reviewed, or for which further RF testing should be undertaken. It is envisioned that such an identifying unit 235 may store structural schematics, or other like identifying data regarding the structure under test, to facilitate specific identification of composite components and/or portions of the structure that, based on the compared differences in the RF patterns, may require further investigation regarding structural integrity.

It should be appreciated that there are instances in which the system described above may be employed to generate the reference RF pattern that is indicated above as having been previously stored in, for example, the data recording/storage unit 220 to which the comparator device 230 makes reference for the comparative analysis of the test RF pattern.

Additionally, it should be understood that the procedure outlined in exemplary form above may be repeated at some later time with the same composite structure, or a structurally similar composite structure, to confirm or update the analysis of the differences in the patterns. In such an instance, the compiler device 225 may compile characteristics of newly received RF signals to form a newly compiled test RF pattern. This newly compiled test RF pattern may be made available to the comparator device 230 for comparison to the stored reference RF pattern an earlier compiled and stored test RF pattern. It should be noted that, during any current or subsequent test process, any received RF signal may or may not be recorded for future comparison. In cases where it may be beneficial to do so, however, recording of each iterative test RF pattern may be undertaken to provide, for example, a historic record of the integrity of a particular composite structure or family of related composite structures. Such data need not be stored locally, but rather may be formatted, via an output data formatting device for transmission to an appropriate local or remote data sink 255. In this case, the data sink 255 is envisioned to be a recordable data storage unit that may be remotely placed or otherwise include a replaceable data storage medium by which data regarding RF signal patterns and analysis of those signal patterns may be storable for future use. Otherwise, the output formatting device 245 may be employed to output any data recorded, compared, analyzed, stored, identified, or intended to be reported from the exemplary RF signal analysis unit 200. The output data formatting device 245 is intended to format any data to be output in a manner compatible to a specific data sink 255. In addition to, for example, external memory storage devices as mentioned above, the output data sink 255 may comprise a display unit or graphical user interface, or like device, and/or an image forming device for respectively temporarily displaying output data and/or generating hard-copy output data.

It should be appreciated that the data recording/storage unit may comprise one or more data storage devices. These one or more data storage devices may be available to store any manner of system information; system control information; recorded information regarding system operation; recorded information regarding raw RF signal data and/or RF signal patterns; data regarding previously-measured/analyzed/compiled reference RF patterns and test RF patterns; data input to the system via, for example, the user interface 210 and/or the input interface 205; data to be output from the system via, for example, the reporting device 240 and/or data sink 255, as described above; or any other manner of system, data and/or control information which may be provided to the system, stored within the system, or output from the system to carry into effect the method for RF signal pattern analysis according to this disclosure.

It should be further appreciated that data formatted for, and output to, any manner of data sink 255 and/or reporting device 240 may be available for real-time analysis, delayed analysis, trend analysis and/or to any other purpose for which such information may be beneficially stored and/or later displayed.

It should be further appreciated that the data recording/storage unit 220 and the controller/processor 215 may respectively or cooperatively provide sufficient data storage and processing capacity to facilitate the inclusion of additional features and/or functionalities to be implemented within the RF signal analysis unit 200. Software applications to facilitate, for example, such other functionalities may be pre-stored within the RF signal analysis unit 200, or communicated to the RF signal analysis unit 200 via the input interface 205, the user interface 210 or otherwise.

Any data storage contemplated for various exemplary embodiments of the disclosed system may be implemented using any appropriate combination of alterable memory or fixed memory. The alterable memory, whether volatile or non-volatile, may be implemented using any one or more of static or dynamic RAM, or for example, any internal disk drive with associated disk type data storage medium, hard drives, flash memories, or any other like memory medium and/or device. Similarly, fixed memory can be implemented using any one or more of ROM, PROM, E-PROM, EE-PROM or compatible disk drive with associated disk type data storage medium, or any other like memory storage medium and/or device. It should be appreciated that the data storage contemplated is not intended to be limited to any specific data storage medium. All currently available data storage capabilities, and reasonable improvements thereon, are considered to be within the scope of the data storage capability contemplated to be implemented in the systems and methods according to this disclosure.

It should be appreciated that given the required inputs, particularly in the form of raw, semi-raw, or initially-processed RF signal data, and location data for one or more RF signal detection units, the processing carried on by the system outlined above, or as described in an exemplary implementation of a method below, may be implemented through software algorithms, hardware or firmware circuits, or any combination of software, hardware and/or firmware control and/or processing elements. Such implementation may include, but not be limited to compilation of RF signal information for RF signal pattern development, comparison of a test RF pattern to a reference RF pattern, identification of areas, or components, of a composite material manufactured structure that may require further investigation and/or replacement based on RF signal and/or pattern comparison.

It should further be appreciated that, although depicted in FIG. 2 as a single RF signal analysis unit 200 incorporating the several depicted internal devices and/or units, the above-described functionalities for receiving input data, to include RF signal data; compiling such data into a test RF pattern; referencing stored informational databases; executing a comparison of the test information with the stored information; providing an identification based on that comparison; and/or outputting to a data sink compatible data for reference may occur with the applicable functionalities being housed within combination devices or individual devices that are not necessarily internal to and/or in any manner integral to the depicted RF signal analysis unit 200. Rather, each of the described functionalities of at least an input interface 205, user interface 210, a controller/processor 215, a data recording/storage unit 220, a compiler device 225, a comparator 230, an identifying unit 235, a reporting device 240, an output data formatting device 245, and a data sink 255 may be implemented as one or more external devices to the RF signal analysis unit 200, as depicted. It should be appreciated that each of the one or more devices and/or units with the exemplary capabilities described as being associated with each of the one or more devices and/or units, may be implemented through any manner of data exchanging communication with the exemplary RF data analysis unit 200. Such communication may include, for example, any manner of wired, wireless, optical and/or other data transmission/reception capability that may be implemented between individual data processing devices and/or units.

Figure 3:
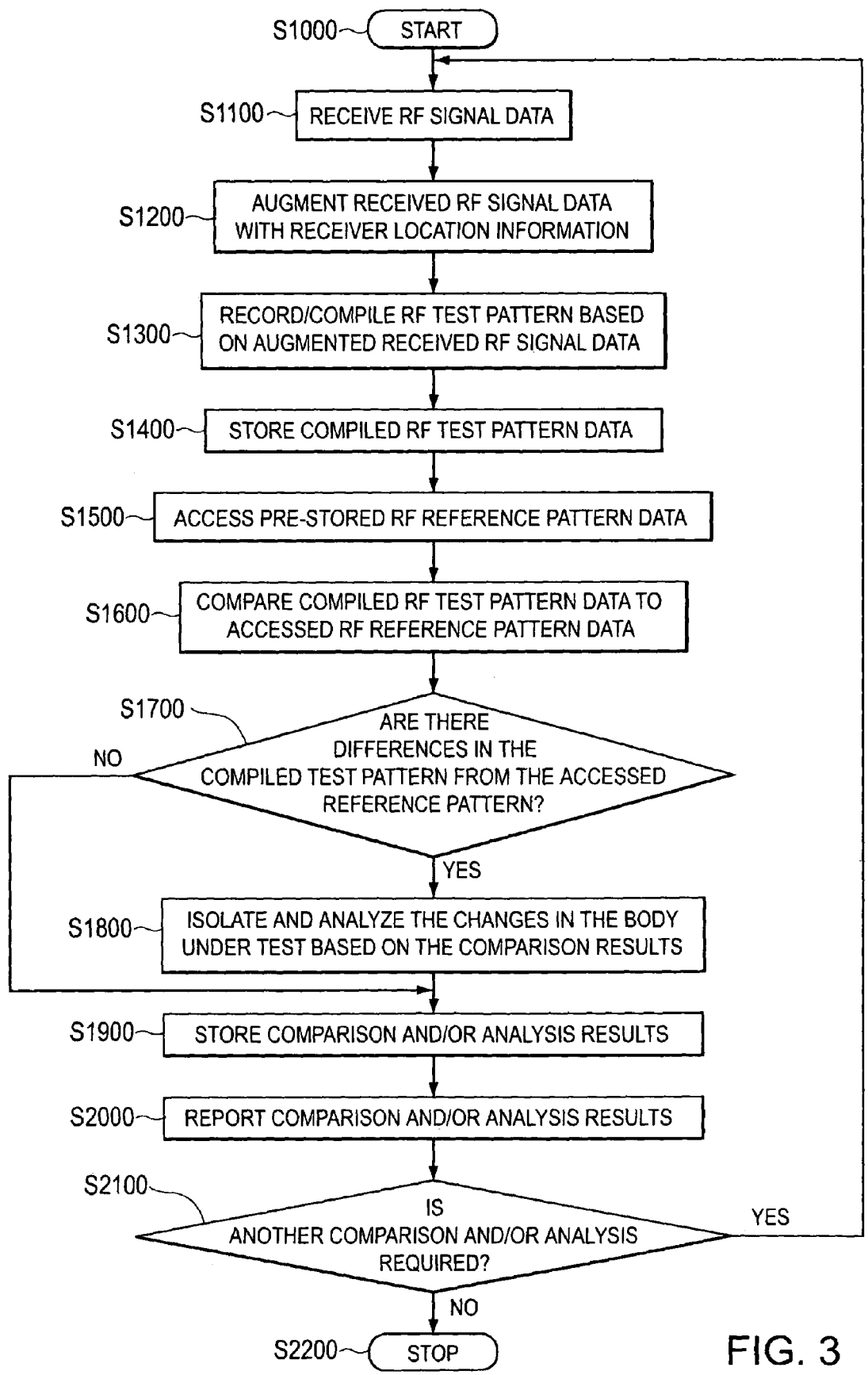
FIG. 3 is a flowchart illustrating an exemplary method for detecting changes in composite structures using RF signals according to this disclosure.

FIG. 3 is a flowchart illustrating an exemplary method for detecting changes in composite structures using RF signals. Operation of the method commences at Step S1000 and continues to Step S1100.

In Step S1100 and RF signal being transmitted from, or in proximity to, a structure partially, or completely, manufactured of composite materials, or otherwise including composite material manufactured components, is received by one or more RF signal detection units. Operation of the method continues to Step S1200.

In Step S1200, received RF signal data is augmented with information regarding location of the RF signal detection unit with respect to the involved composite structure, and/or the RF signal transmitter, in as many as three dimensions. This information is necessary such that raw, or potentially data-converted, RF signal data includes some spatial reference to the involved composite structure under test. Operation of the method continues to Step S1300.

It should be appreciated that information regarding the positioning, fixed or mobile, of one or more RF signal detection units may be provided by the individual RF signal detection unit, or be stored within, for example, an RF signal analysis unit that stores information regarding predetermined positioning of individual RF signal detection units with respect to a system reference.

In Step S1300, received RF signal data properly augmented with location information for the individual RF signal detection units, may be recorded and/or otherwise compiled to provide one or more local discrete test RF signal patterns, or a complete test RF signal pattern, for a portion of, or an entire, composite structure under test. Operation of the method continues to Step S1400.

In Step S1400, the recorded/compiled test RF pattern may be optionally stored in any manner of data storage device to be later recalled for any beneficial purpose. Such beneficial purposes include, but are not limited to, trend analysis regarding the integrity of the composite structure under test, or comparative analysis between a family of composite structures, or specific areas and/or components within a structure that are formed of composite materials. Operation of the method continues to Step S1500.

In Step S1500, pre-stored reference RF signal pattern data for the composite structure under test is accessed. Operation of the method continues to Step S1600.

In Step S1600, compiled test RF signal pattern data, whether stored or not, is compared with accessed pre-stored reference RF signal pattern data to assess changes between the reference RF signal pattern data regarding the composite structure under test and the test RF signal pattern data for the composite structure under test. Operation of the method continues to Step S1700.

In Step S1700 a determination is made whether there are differences detected between the reference RF signal pattern data and the test RF signal pattern data for the composite structure under test. If in Step S1700, a determination is made that there are no differences, operation of the method continues to optional Steps S1900 or S2000 or directly to Step S2100.

If in Step S1700, a determination is made that there are differences between the reference RF signal pattern data and the test RF signal pattern data for the composite structure under test, operation of the method continues to Step S1800.

It should be appreciated that the above determination may not be based on an absolute comparison between the reference RF signal pattern and the test RF signal pattern. Rather, some threshold for an acceptable level of change may be established or otherwise pre-determined. In such an instance, only if such an established threshold is exceeded would the criteria for the determination in Step S1700 be met.

In Step S1800, areas where changes in the composite structure may exist based on analysis of differences between the reference RF signal pattern data and the test RF signal pattern data are identified and isolated. Operation of the method may continue to optional Steps S1900 or S2000, or directly to Step S2100.

In optional Step S1900, any results regarding detected differences in the RF signal pattern data, and/or identification and isolation of changes in a composite structure under test based on the comparative analysis between versions of RF signal pattern data may be optionally stored to be later used to any beneficial purpose. Operation of the method continues to optional Step S2000, or directly to Step S2100.

In optional Step S2000, any results of the comparative analysis and/or the identification and isolation of changes in physical structure of the composite structure under test based on analysis of the differences in the RF pattern data may be formatted and reported externally by any manner of data reporting device. Data reporting methodologies may include, but are not limited to, outputting data to a data sink such as, for example, a data display, a graphical user interface, or an image forming device to create a hard-copy image of the data, or remote transmission to a compatible receiving node for off-site analysis of the reported results. Operation of the method continues to Step S2100.

In Step S2100, a determination is made whether another analysis and/or comparison is required. If in Step S2100 a determination is made that another analysis and/or comparison is required, operation of the method reverts to an appropriate step to re-commence receiving, augmenting, recording/compiling, storing, accessing, or comparing current RF signal data, as described above.

If in Step S2100, a determination is made that no further comparison and/or analysis is required operation of the method continues to Step S2200 where operation of the method ceases.

It should be appreciated that at least the Steps S1100-S1400 above may be alternatively employed to compile the pre-stored RF reference pattern data when such steps are undertaken with respect to a known or new or otherwise control composite structure. In instances where the systems and methods according to this disclosure are to be used to monitor the integrity of the composite materials within a composite structure over time, the pre-stored RF reference pattern data will be based on an initial RF examination of the composite structure employing Steps S1100-S1400 as described above.

While exemplary embodiments have been described above for the disclosed systems and methods, the exemplary embodiments and variations thereof should be viewed as illustrative, and not limiting. Various modifications, substitutes, or the like may be possible to implement the systems and methods according to this disclosure, and such variations are reasonably contemplated by reference to the above discussed exemplary embodiments.

What is claimed is:

1. A method for detecting changes in composite structures, comprising:
   detecting at least one RF signal transmitted from an RF transmitter located in a structure including at least one composite material or composite component;
   compiling characteristics of the at least one detected RF signal;
   generating a test RF pattern based on the characteristics of the at least one detected RF signal;
   accessing at least one reference RF pattern related to the structure;
   comparing the reference RF pattern with the test RF pattern to determine differences in the characteristics of the test RF pattern; and
   identifying changes in the at least one composite material or composite component of the structure based on the pattern comparison.

2. The method of claim 1, wherein detecting the at least one RF signal comprises employing at least one RF detection unit located proximately to the composite structure, the position of the at least one RF detection unit being at least one of known or calculated with regard to a reference position of the composite structure.

3. The method of claim 2, wherein the at least one of the known or the calculated position of the RF detection unit is used in compiling characteristics of the at least one detected RF signal.

4. The method of claim 1, wherein the at least one reference RF pattern is provided for the composite structure or for a related composite structure.

5. The method of claim 1, wherein accessing the at least one reference RF pattern comprises reading data regarding the at least one reference RF pattern from at least one of a data storage unit, device or medium where the data regarding the at least one reference RF pattern is pre-stored.

6. The method of claim 1, wherein another RF transmitter is located proximately to the composite structure and the detecting at least one RF signal comprises detecting an RF signal transmitted from the another RF transmitter.

7. The method of claim 1, further comprising outputting the results of at least one of the comparing, isolating or identifying to at least one of a data sink or a data reporting device.

8. The method of claim 1, further comprising storing the test RF pattern.

9. The method of claim 8, further comprising:
   detecting at least a second RF signal transmitted from the RF transmitter located in a structure including at least one composite material or composite component at another time;
   compiling characteristics of the at least second detected RF signal;
   generating a second test RF pattern based on the characteristics of the at least second detected RF signal;
   accessing at least one of the reference RF pattern related to the structure or the stored test RF pattern;
   comparing the accessed at least one of the reference RF pattern or the stored test RF pattern with the second test RF pattern to determine differences in the characteristics of the second test RF pattern; and
   at least one of isolating or identifying changes in the at least one composite material or composite component of the structure based on the pattern comparison.

10. The method of claim 1, wherein the composite structure is at least one of an aircraft or a spacecraft.

11. A computer-readable data storage medium on which is stored a program for implementing the method according to claim 1.

12. A method for establishing a reference RF pattern for a composite structure comprising:
   detecting at least one RF signal transmitted from an RF transmitter located in a
   known baseline structure including at least one composite material or composite component; compiling characteristics of the at least one detected RF signal; generating a reference RF pattern for the at least one composite material or component in the known baseline structure based on the characteristics of the at least one detected RF signal;
   comparing the reference RF pattern with the test RF pattern to determine differences in the characteristics of the test RF pattern; and
   identifying changes in the at least one composite material or composite component of the structure based on the pattern comparison.

13. A system for detecting changes in composite structures, comprising:
   an RF receiver that receives at least one RF signal transmitted from an RF transmitter located in a structure including at least one composite material or composite component;
   a compiler device that compiles characteristics of the at least one detected RF signal and generates a test RF pattern based on the characteristics of the at least one detected RF signal;
   a storage unit that stores at least one reference RF pattern related to the structure;
   a comparator device that accesses the at least one reference RF pattern and compares the reference RF pattern and the test RF pattern to determine differences in the characteristics of the reference RF pattern and test RF pattern; and
   an identifying unit that identifies changes in the at least one composite material or composite component of the structure based on the pattern comparison.

14. The system of claim 13, wherein the RF receiver further comprises at least one RF detection unit located proximately to the composite structure, the position of the at least one RF detection unit being at least one of known or calculated with regard to a reference position of the composite structure.

15. The system of claim 14, wherein the at least one RF detection unit is movable with respect to the reference position of the composite structure.

16. The system of claim 14, wherein the at least one of the known or the calculated position of the RF detection unit is used in compiling characteristics of the at least one detected RF signal.

17. The system of claim 13, wherein the at least one reference RF pattern is provided for the composite structure or for a related composite structure.

18. The system of claim 13, wherein another RF transmitter is located proximately to the composite structure and the RF receiver receives at least one RF signal transmitted from the another RF transmitter.

19. The system of claim 13, further comprising at least one of a data sink or a data reporting device that is usable to output the results of at least one of the results of the functions of the comparator device or the identifying unit.

20. The system of claim 13, wherein the composite structure is at least one of an aircraft or a spacecraft.

* * * * *